United States Patent [19]

Clinton, deceased et al.

[11] 4,423,065

[45] Dec. 27, 1983

[54] NAPHTHALENAMINE INSECTICIDES

[75] Inventors: Albert J. Clinton, deceased, late of Indianapolis, Ind., by American Fletcher National Bank and Trust Company, Administrator; George O. P. O'Doherty, Greenfield, Ind.

[73] Assignee: Eli Lilly and Company, Indianapolis, Ind.

[21] Appl. No.: 374,802

[22] Filed: May 4, 1982

[51] Int. Cl.³ .................. A01N 37/34; A01N 33/06
[52] U.S. Cl. .................. 424/304; 260/465 E; 564/431; 424/330
[58] Field of Search .................. 424/304, 330; 260/465 E; 564/431

[56] References Cited

U.S. PATENT DOCUMENTS

| | | | |
|---|---|---|---|
| 2,212,825 | 8/1940 | Daudt et al. | 260/571 |
| 4,117,167 | 9/1978 | Barlow et al. | 424/330 |
| 4,183,949 | 1/1980 | Hamprecht et al. | 424/304 |
| 4,304,791 | 12/1981 | Clinton | 424/330 |

FOREIGN PATENT DOCUMENTS 1383523  2/1975  United Kingdom .

*Primary Examiner*—Dolph H. Torrence
*Attorney, Agent, or Firm*—Kathleen R. S. Page; Author R. Whale

[57] ABSTRACT

Substituted-N-[2,4-dinitro-6-(trifluoromethyl)phenyl]-naphthalenamine derivatives useful as insecticides and ectoparasiticides.

36 Claims, No Drawings

NAPHTHALENAMINE INSECTICIDES

SUMMARY OF THE INVENTION

The present invention relates to a method for suppressing insects which comprises applying to a locus of the insects an insecticidally-effective amount of a compound of the formula

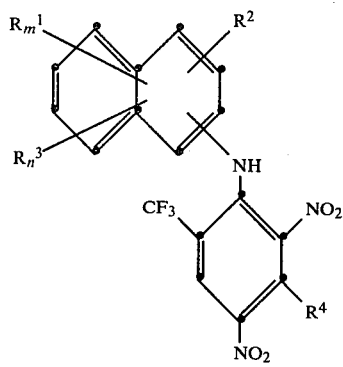

wherein:
$R^1$ is $C_1$-$C_4$ alkyl;
$R^2$ is halogen, phenyl, nitro, cyano, $C_1$-$C_4$ fluoroalkyl, $C_1$-$C_4$ fluoroalkoxy or $C_1$-$C_4$ fluoroalkylthio;
$R^3$ is halogen;
$R^4$ is hydrogen or halogen;
m is 0, 1 or 2; and
n is 0 or 1;
with the proviso that $R^2$ and the dinitroaniline moiety are on the same ring.

Also provided by this invention is a method of killing insects which consume living tissues of a host animal which comprises orally or percutaneously administering to a host animal infested with such insects an ectoparasiticidally-effective amount of a compound of the above formula.

The present invention also relates to a compound of the following three formulas:

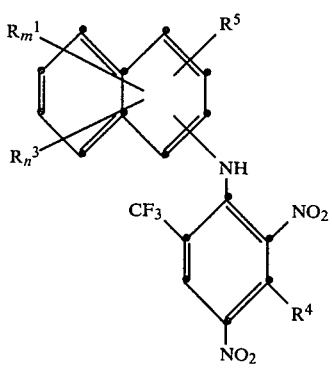

wherein:
$R^1$ is $C_1$-$C_4$ alkyl;
$R^3$ is halogen;
$R^4$ is hydrogen or halogen;
$R^5$ is phenyl, nitro or cyano;
m is 0, 1 or 2; and
n is 0 or 1;

with the proviso that $R^5$ and the dinitroaniline moiety are on the same ring;

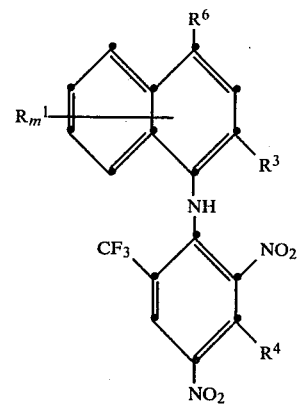

wherein:
$R^1$ is $C_1$-$C_4$ alkyl;
$R^3$ is halogen;
$R^4$ is hydrogen or halogen;
$R^6$ is halogen, $C_1$-$C_4$ fluoroalkyl, $C_1$-$C_4$ fluoroalkoxy or $C_1$-$C_4$ fluoroalkylthio; and
m is 0, 1 or 2;

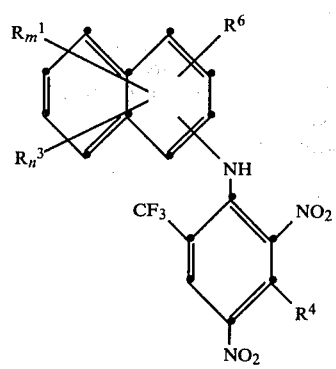

wherein:
$R^1$ is $C_1$-$C_4$ alkyl;
$R^3$ is halogen;
$R^4$ is hydrogen or halogen;
$R^6$ is halogen, $C_1$-$C_4$ fluoroalkyl, $C_1$-$C_4$ fluoroalkoxy or $C_1$-$C_4$ fluoroalkylthio;
m is 0, 1 or 2; and
n is 0 or 1;
with the provisos that $R^6$ and the dinitroaniline moiety are on the same ring and simultaneously occur at other than the 1 and 4 positions.

Preferred compounds employed in the present invention have the above formula wherein m is 0 and $R^4$ is hydrogen.

DETAILED DESCRIPTION OF THE INVENTION

In the above formula, $C_1$-$C_4$ alkyl includes methyl, ethyl, n-propyl, isopropyl, N-butyl, sec.-butyl, isobutyl, t-butyl, and the like.

The term "halogen" represents fluorine, chlorine, bromine and iodine.

$C_1$-$C_4$ Fluoroalkyl is a $C_1$-$C_4$ alkyl group bearing one or more fluorine atoms. Such fluoroalkyl groups include trifluoromethyl, 1,1,2,2-tetrafluoroethyl, pentafluoroethyl, 1,2,3,3-tetrafluoropropyl, nonafluorobutyl, and the like.

$C_1$–$C_4$ Fluoroalkoxy is a $C_1$–$C_4$ alkoxy group bearing one or more fluorine atoms. Such fluoroalkoxy groups include difluoromethoxy, trifluoromethoxy, 1-fluoroethoxy, 1,1,2,2-tetrafluoroethoxy, pentafluoroethoxy, 1,2,2,3,3-pentafluoropropoxy, heptafluoropropoxy, 4,4,4-trifluorobutoxy, and the like.

$C_1$–$C_4$ Fluoroalkylthio is a $C_1$–$C_4$ alkylthio group bearing one or more fluorine atoms. Such fluoroalkylthio groups include trifluoromethylthio, 1,1,2,2-tetrafluoroethylthio, pentafluoroethylthio, 4,4,4-trifluorobutylthio, and the like.

The compounds listed below are typical of the compounds employed in the present invention. It will be understood that the compounds specifically named herein do not bound the scope of compounds provided by the method of the invention, but are presented merely to assure that those skilled in the art will fully understand this invention.

1-Cyano-N-[2,4-dinitro-6-(trifluoromethyl)phenyl]-3-naphthalenamine 1-(1,1,2,2-Tetrafluoroethoxy)-6-chloro-N-[2,4-dinitro-6-(trifluoromethyl)phenyl]-2-naphthalenamine 3-Bromo-6-ethyl-N-[2,4-dinitro-3-chloro-6-(trifluoromethyl)phenyl]-1-naphthalenamine 4-(Trifluoromethoxy)-7-bromo-N-[2,4-dinitro-6-(trifluoromethyl)phenyl]-1-naphthalenamine The compounds of the present invention may be conveniently prepared by methods well known to those skilled in the art. The preferred method of preparation involves condensing an appropriately substituted naphthalene derivative with a 2,4-dinitro-6-(trifluoromethyl)-1-(substituted)benzene derivative in the presence of a base to give a present napthalenamine. The scheme for this reaction is as follows:

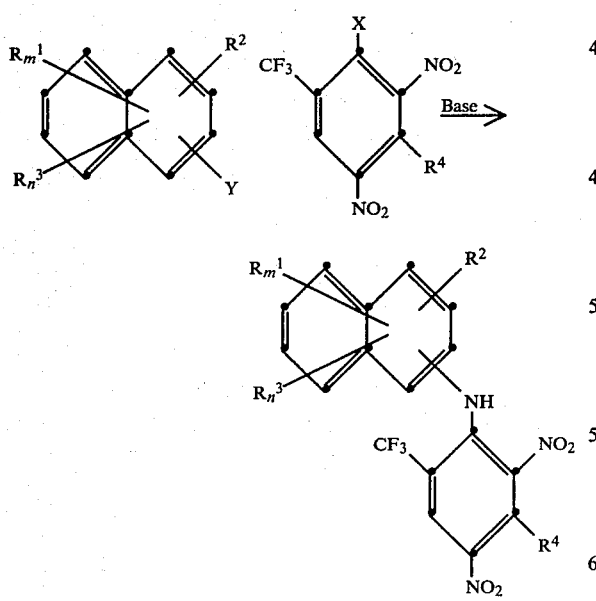

wherein $R^1$, $R^2$, $R^3$, $R^4$, m and n are as defined above, and one of X and Y is $NH_2$ and the other is a good leaving group such as halogen.

An example of this reaction scheme involves reacting a 1-naphthalenamine derivative with a halobenzene derivative. This reaction is generally performed by combining approximately equimolar quantities of the naphthalenamine and substituted halobenzene derivatives with at least one equivalent of base in a suitable organic solvent. Suitable solvents should be unreactive and include most aprotic solvents. Commonly used solvents include amides, for instance, N,N-dimethylformamide or hexamethylphosphoramide; ethers, such as tetrahydrofuran, diethyl ether and dioxane; sulfoxides, such as dimethyl sulfoxide; and related solvents. Of these, DMF is preferred.

The reaction is usually performed at a temperature in the range of from about $-25°$ C. to $100°$ C., with $0°$ C. to $50°$ C. being preferred. The base used as a reactant should preferably be of sufficient strength to pull the nitrogen proton of the naphthalenamine derivative. Suitable bases include most of the alkali metal hydrides, for example sodium hydride and lithium hydride. Sodium hydride is preferred. Following formation of the product, which usually occurs nearly immediately to after about 48 hours, the mixture is worked up according to standard procedures. Typically, the product may be isolated by simply adding to the reaction mixture either water or an aqueous acid solution, for instance dilute aqueous hydrochloric acid or sulfuric acid. The desired product often precipitates out of the aqueous acid solution as a solid or an oil. Alternatively, the product may be extracted into a water immiscible organic solvent such as diethyl ether, ethyl acetate, dichloromethane, or the like. Removal of the organic solvent, for instance by evaporation under reduced pressure, then provides a compound of this invention. The product thus formed can be further purified if desired by any of several methods well known to those skilled in the art, for example by column chromatography over silica gel or crystallization from common solvents.

The compounds employed in the present invention are preferably prepared by condensing the substituted benzene and naphthalene starting materials as intact compounds each with its substituents already in place. These starting materials are readily prepared by well known procedures. However, certain substituents may be added onto the substituted N-[2,4-dinitro-6-(trifluoromethyl)phenyl]naphthalenamine derivative as well. For example, halogen substituents may be added to the compound at various positions by any of several well known halogenating agents.

The following detailed examples are provided in an effort to more fully illustrate specific aspects of this invention. The examples are not intended to be limiting in any respect and should not be so construed.

EXAMPLE 1

1-Nitro-N-[2,4-dinitro-6-(trifluoromethyl)phenyl]-2-naphthalenamine

To a slurry of 2.0 g. of sodium hydride and 40 ml. DMF was added 3.8 g. of 1-nitro-2-naphthalenamine. Next, 5.4 g. of 2,4-dinitro-6-(trifluoromethyl)-1-chlorobenzene was added to the reaction mixture which was allowed to stir at room temperature for about one hour. The mixture was added to 500 ml. ice water containing 40 ml. of concentrated hydrochloric acid. The yellow precipitate was collected by filtration and dried to afford 4.8 g. of 1-nitro-N-[2,4-dinitro-6-(trifluoromethyl)phenyl]-2-naphthalenamine. Yield 56%. M.P.=$213°$–$215°$ C.

Analysis calculated for $C_{17}H_9F_3N_4O_6$: Theory: C, 48.35; H, 2.15; N, 13.27; Found: C, 48.54; H, 2.21; N, 13.35.

EXAMPLE 2

4-Chloro-N-[2,4-dinitro-6-(trifluoromethyl)phenyl]-1-naphthalenamine

Two grams of sodium hydride were slowly added to a stirring solution of 3.5 g. of 4-chloro-1-naphthalenamine and 5.4 g. of 2,4-dinitro-6-(trifluoromethyl)-1-chlorobenzene dissolved in 30 ml. of DMF. The reaction mixture was stirred at room temperature for approximately 24 hours and poured into water. The precipitated solid was collected by filtration and recrystallized from ethanol to afford 4.7 g. of 4-chloro-N-[2,4-dinitro-6-(trifluoromethyl)phenyl]-1-naphthalenamine. Yield 57%. M.P.=197°-198° C.

Analysis calculated for $C_{17}H_9ClF_3N_3O_4$: Theory: C, 49.59, H, 2.20; N, 10.21; Found: C, 49.31; H, 2.10; N, 10.07.

EXAMPLE 3

2-Bromo-4-chloro-N-[2,4-dinitro-6-(trifluoromethyl)phenyl]-1-naphthalenamine To a solution of 2.0 g. of 4-chloro-N-[2,4-dinitro-6-(trifluoromethyl)phenyl]-1-naphthalenamine dissolved in 30 ml. dichloromethane was added 1 ml. of bromine. The mixture was stirred at room temperature for about two and one-half hours and evaporated to dryness under reduced pressure. The residue was dissolved in a diethyl ether/ethyl acetate solution and washed with water. The organic phase was combined with charcoal and anhydrous magnesium sulfate, stirred and filtered. The solvents were evaporated under reduced pressure, stirred with Skellysolve B and filtered to provide 1.5 g. of 2-bromo-4-chloro-N-[2,4-dinitro-6-(trifluoromethyl)phenyl]-1-naphthalenamine. Yield 63%. M.P.=207°-209° C.

Analysis calculated for $C_{17}H_8BrClF_3N_3O_4$: Theory: C, 41.61; H, 1.64; N, 8.57; Found: C, 41.69; H, 1.71; N, 8.65.

The following examples further illustrate the compounds employed in the present invention and were prepared by the general procedures outlined above.

EXAMPLE 4

4-Bromo-N-[2,4-dinitro-6-(trifluoromethyl)phenyl]-1-naphthalenamine

M.P.=219°-221° C.

Analysis calculated for $C_{17}H_9BrF_3N_3O_4$: Theory: C, 44.74; H, 1.97; N, 9.21; Found: C, 45.35; H, 1.70; N, 9.33.

EXAMPLE 5

4-Phenyl-N-[2,4-dinitro-6-(trifluoromethyl)phenyl]-1-naphthalenamine

M.P.=161°-162° C.

Analysis calculated for $C_{23}H_{14}F_3N_3O_4$: Theory: C, 60.93; H, 3.11; N, 9.27; Found: C, 62.32; H, 3.07; N, 9.26.

EXAMPLE 6

4-Nitro-N-[2,4-dinitro-6-(trifluoromethyl)phenyl]-1-naphthalenamine

M.P.=166°-168° C.

Analysis calculated for $C_{17}H_9F_3N_4O_6$: Theory: C, 48.35; H, 2.15; N, 13.27; Found: C, 48.59; H, 2.20; N, 13.23.

EXAMPLE 7

4-Cyano-N-[2,4-dinitro-6-(trifluoromethyl)phenyl]-1-naphthalenamine

M.P.=174°-175° C.

Analysis calculated for $C_{18}H_9F_3N_4O_4$: Theory: C, 53.74; H, 2,26; N, 13.93; Found: C, 53.66; H, 2,27; N, 14.11.

EXAMPLE 8

2,4-Dibromo-N-[2,4-dinitro-6-(trifluoromethyl)phenyl]-1-naphthalenamine

M.P. 197°-200° C.

Analysis calculated for $C_{17}H_8Br_2F_3N_3O_4$:
Theory: C, 38.13; H, 1.50; N, 7,85; Found: C, 38.39; H, 1.55; N, 7.56.

The compounds employed in the present invention are useful for the control of insects of various orders, including Coleoptera such as Mexican bean beetle, boll weevil, corn rootworm, cereal leaf beetle, borers, flea beetle, Colorado potato beetle, grain beetle, alfalfa weevil, carpet beetle, confused flour beetle, powder post beetle, wireworms, rice weevil, rose beetle, plum curculio and white gribbs; Lepidoptera such as southern armyworm, codling moth, cutworm, clothes moth, Indian meal moth, leaf rollers, corn earworm, European corn borer, cabbage worm, cabbage looper, cotton bollworm, bagworm, eastern tent caterpillar, sod webworm and fall armyworm; Diptera such as housefly, yellow fever mosquito, stable fly, horn fly, blowfly, cabbage maggot and carrot rust fly; and Orthoptera such as German cockroach and American cockroach.

Therefore it is provided as one embodiment of the present invention a method for suppressing insects which comprises applying to a locus of the insects an insecticidally-effective amount of a present naphthalenamine derivative. The term "insecticidally-effective amount," as defined herein, refers to an amount which results in the inactivation of the insect. Such inactivation can kill the insect or render the insect incapable of performing one or more of its normal life functions. This amount will generally be from about 10,000 ppm to about 1 ppm, more preferably from about 1000 ppm to about 10 ppm. It is apparent that higher or lower concentrations can be employed depending on such factors as the insect species to be controlled, the locus to which the application is to be made, the potency of the particular naphthalenamine employed, and the like.

The compounds employed in the present invention appear to function most effectively when the treated plants contact the insect for which control or eradication is desired. Generally, however the compounds may be applied to any food or water source which the insects may either ingest or contact by other than eating.

It is also believed that the compounds may interfere with the mechanism of metamorphosis which occurs in the insect. However, the precise mechanism by which the present naphthalenamines act is not yet known, and the insecticidal method of the present invention is not limited by any mode of operation.

The compounds employed in the present invention are preferably formulated for ease of application. Therefore, as yet another embodiment of the present invention, a composition comprising an agriculturally-acceptable carrier or diluent together with a present naphthalenamine are disclosed. Such compositions will typically contain from about 0.1 to about 95.0 percent by weight of a naphthalenamine depending on the composition desired.

Liquid compositions, for example emulsifiable concentrates and aqueous suspensions, will contain the active agent at a concentration of from about 5 to about 90 percent by weight. These compositions are prepared by dissolving the substance in an organic liquid or by dispersing the substance in water with or without the aid of a suitable surface-active dispersing agent such as an ionic or nonionic emulsifying agent. Such compositions also can contain substances which serve to aid spreading and adhesion of the material on plant foliage. Suitable organic liquid carriers include the agricultural spray oils and the petroleum distillates such as diesel fuel, kerosene, fuel oil, naphthas, and Stoddard solvent. Ot these, the petroleum distillates are generally preferred. The aqueous compositions can contain one or more water-immiscible solvents. In such aqueous compositions, the carrier comprises an aqueous emulsion, e.g., mixture of water, emulsifying agents, and water-immiscible solvents. The choice of dispersing and emulsifying agent and the amount thereof employed will depend on the nature of the composition and the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface active agents which are suitable for use in the above discribed compositions see U.S. Pat. No. 3,095,299, second column, lines 25–36, and references cited therein.

A wettable powder will comprise an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed naphthalenesulfonates, and the alkyl sulfates.

Dust compositions will contain an active agent in an amount from about 0.1 to about 10.0 percent by weight. In the preparation of dust compositions, the active ingredient is intimately dispersed in and on a finely-divided solid such as clay, talc, chalk, gypsum, limestone, vermiculite fines, perlite, and the like. In one method of achieving such dispersion, the finely-divided carrier is mechanically mixed or ground with the active agent. Similarly, dust compositions can also be combined with various solid carriers such as bentonite, fuller's earth, attapulgite, and other clays having surface-active adsorptive properties. Depending upon the proportions of ingredients, these dust compositions can be employed as concentrates and subsequently diluted with additional adsortive-type solid carriers or with chalk, talc, or gypsum, or the like usually at the site of application. Also, such dust compositions can be dispersed in water, with or without the aid of a dispersing agent, or from spray mixtures.

Also the compositions of the present invention can be employed in granular formulations containing from about 0.1 to 15 percent by weight of a present naphthalenamine. These formulations are prepared in conventional manner, typically by dissolving the compound in a solvent with or without a surface-active agent and spraying or otherwise distributing the resulting solution onto pre-formed granules. The solvent is then usually evaporated to provide a suitable composition. Such granular formulations are capable of providing longer-lasting activity and may be preferred for crops such as corn where repeated application is not practical.

A compound of the present invention, or a composition thereof, may be applied to the locus for which insecticidal control is desired by any of several conventional methods familar to those skilled in the art. Common application techniques include hand dusting or spraying, or by simply mixing the active agent with the insect's food. Application to the foliage of plants is typically performed with power dusters, boom sprayers, and fog sprayers. In larger scale operations, dust or low volume sprays can be applied from the air.

The insecticidal efficacy of representative compounds employed in the present invention is illustrated by the following experiments.

EXPERIMENT 1

This initial screen was used to evaluate the insecticidal efficacy of representative compounds employed in the present invention. Evaluations were made against yellow fever mosquito larvae.

The test compounds were formulated by dissolving 20 mg. of the compound into 2 ml. of solvent. The solvent was prepared by placing Toximul R and Toximul S (proprietary blends of anionic and nonionic surfactants manufactured by Stepan Chemical Company, Northfield, Ill.) into a 50/50 mixture of acetone/ethanol. The solvent/compound solution was diluted to 8 ml. with deionized water. The formulated compound was then placed in 225 ml. water.

Twenty late third or early fourth instar mosquito larvae (*Aedes aegypti*) were placed in a one ounce paper cup containing 25 ml. of deionized water. The larvae were allowed to feed on fresh food for at least three hours prior to being placed on test. This water containing larvae was then added to the diluted compound formulation to provide a final concentration of 20 ppm. of active ingredient. Lower concentrations were obtained by further dilution with water.

The number of dead or moribund larvae were then recorded 48 hours later. Moribund larvae are those only capable of limited, or poorly coordinated, locomotion. The results were rated by the following code:

| Number Dead or Moribund Larvae | Percent | Rating |
| --- | --- | --- |
| 0–2 | 0–10 | 0 |
| 3–4 | 11–20 | 1 |
| 5–6 | 21–30 | 2 |
| 7–8 | 31–40 | 3 |
| 9–10 | 41–50 | 4 |
| 11–12 | 51–60 | 5 |
| 13–14 | 61–70 | 6 |
| 15–16 | 71–80 | 7 |
| 17–18 | 81–90 | 8 |
| 19–20 | 91–100 | 9 |

The results of this screen appear below in Table 1.

TABLE 1

Mosquito Larvicide Screen

| Example No. of Compound Tested | Concentration (ppm) | Rating |
| --- | --- | --- |
| 1 | 20.0 | 6 |
| 2 | 20.0 | 9 |
|   | 0.1 | 4 |
| 3 | 20.0 | 9 |
|   | 0.1 | 9 |
|   | 0.01 | 7 |
|   | 0.005 | 3 |
| 4 | 20.0 | 9 |
| 5 | 20.0 | 8 |
| 6 | 20.0 | 9 |
| 7 | 20.0 | 9 |
| 8 | 20.0 | 9 |
|   | 0.1 | 9 |
|   | 0.01 | 9 |
|   | 0.005 | 9 |
|   | 0.005 | 7 |
|   | 0.003 | 6 |
|   | 0.003 | 7 |
|   | 0.001 | 0 |

EXPERIMENT 2

Compounds evaluated in this screen were formulated by dissolving 10 mg. of the compound in one ml. of solvent as prepared above in Experiment 1. The solvent/compound mixture was diluted with 9 ml. of deionized water to provide a 1000 ppm test compound concentration. Lower concentration formulations were obtained by diluting the 1000 ppm solution with an appropriate volume of water containing 225 mg. of Toximul R and 125 mg. of Toximul S per liter. Evaluations were then made on Mexican bean beetle (*Epilachna varivestis*), southern armyworm (*Prodenia eridania*) and two-spotted spider mite (*Tetranychus uriticae*) according to the following methods.

The method used to evaluate Mexican bean beetle activity involved spraying the leaves of 4- to 6-day old Bountiful green bean plants with the test formulation. After the leaves had dried, one leaf was removed from the plant and the cut end wrapped in water soaked cellucotton. This leaf was placed in a plastic petri dish containing 5 second and third instar Mexican bean beetle larvae. The dishes were maintained in the laboratory for 4 days at which point the number of dead larvae were counted and the amount of feeding was noted. Two replications were performed for each compound.

Activity of the compounds against southern armyworm was determined in substantially the same manner as that described for Mexican bean beetle. In this method, however, 5 third instar southern armyworm larvae were placed in the petri dish containing the treated leaf. Evaluations were made in the same manner as above.

In the final method, bean plants were infested with two-spotted spider mites. After 24 hours a blue hubbard squash plant leaf was infected by placing the bean leaf containing mites on it. After 24 additional hours the infested squash plant leaf was sprayed with the test formulation and maintained for 4 days as above.

For all of the test species, the following rating system was used:

| Rating | % Dead |
| --- | --- |
| 0 | 0 |
| 1 | 1–50 |
| 2 | 51–99 |
| 3 | 100 |

For the beetle and armyworm procedures, when less than half of the leaves were eaten, percent feeding was recorded as follows:

| Rating | Observation |
| --- | --- |
| 0 | none of the leaves were eaten |
| 1 | 1–50% of the leaves were eaten |

The results of this test appear below in Table 2.

TABLE 2

Mite-Insect Screen

| Example No. of Compound Tested | Concentration ppm | Mexican Bean Beetle | | Southern Armyworm | | Two-spotted spider mite |
| --- | --- | --- | --- | --- | --- | --- |
| | | Stomach | Feeding | Stomach | feeding | Contact |
| 1 | 1000 | 3 | 0 | 0 | | 0 |
| | | 3 | 1 | 0 | | |
| | | 0 | | | | |
| | 100 | 1 | | | | |
| | | 0 | | | | |
| 2 | 1000 | 3 | 1 | 3 | 1 | 0 |
| | | 3 | 1 | 3 | 0 | |
| | | 3 | 1 | 3 | 1 | |
| | | 3 | 0 | 3 | 1 | |
| | 100 | 2 | | 0 | | |
| | | 3 | | 0 | | |
| 3 | 1000 | 2 | 1 | 3 | 0 | 0 |
| | | 3 | 1 | 3 | 0 | |
| | | 3 | 0 | 3 | 0 | |
| | | 3 | 0 | 3 | 1 | |
| | 100 | 1 | | 0 | | |
| | | 1 | | 0 | | |
| 4 | 1000 | 0 | | 1 | | |
| | | 0 | | 1 | | |
| 5 | 1000 | 3 | 1 | 0 | | 0 |
| | | 3 | 1 | 0 | | |
| | | 3 | | | | |
| | | 3 | | | | |
| | 100 | 3 | 1 | | | |
| | | 3 | 0 | | | |
| | | 3 | 0 | | | |
| | | 3 | 0 | | | |

TABLE 2-continued

| Example No. of Compound Tested | Concentration ppm | Mite-Insect Screen | | | | |
|---|---|---|---|---|---|---|
| | | Mexican Bean Beetle | | Southern Armyworm | | Two-spotted spider mite |
| | | Stomach | Feeding | Stomach | feeding | Contact |
| | 10 | 0 | | | | |
| | | 0 | | | | |
| 6 | 1000 | 3 | 1 | 0 | | 0 |
| | | 3 | 0 | 0 | | |
| | | 3 | 0 | | | |
| | | 3 | 0 | | | |
| | 100 | 2 | | | | |
| | | 1 | | | | |
| 7 | 1000 | 2 | 0 | 3 | 0 | 0 |
| | | 3 | 0 | 3 | 0 | |
| | | 3 | 0 | 3 | 0 | |
| | | 3 | 0 | 3 | 0 | |
| | 100 | 3 | 0 | 0 | | |
| | | 3 | 0 | 0 | | |
| | | 0 | | | | |
| | | 0 | | | | |
| | 10 | 0 | 0 | | | |
| | | 0 | 0 | | | |

The compounds employed in the present invention have also displayed activity as ectoparasiticides. Therefore an additional locus to which an insecticidally-effective amount of a present naphthalenamine may be applied is the exterior of the insect host animal. The compounds appear to function most effectively when applied to the exterior of the host animal, so that insects contacting the exterior surface of the animal will be thereby controlled. Effective insect control is achieved for the compounds when used as ectoparasiticides at rates similar to those described above for insecticides generally.

When used as ectoparasiticides it is preferable to formulate the compounds prior to application. The compounds are generally formulated for dermal or topical administration according to the general procedures outlined above for insecticides generally.

The formulated compounds are applied to host animals by procedures conventional in agricultural chemistry. For example, liquid compositions may be simply sprayed on the animals for which insecticidal control is desired. The animals may also treat themselves by such devices as back rubbers, which may contain the toxicant compound in a cloth, for example, which the animal may walk against and contact; and dust bags, which the animal may bump against thereby dislodging a dust containing the active ingredient. Dip tanks are also employed to administer the active agent to the host animal. According to this procedure, the parts of the animal's body for which insecticidal control is desired are simply immersed in a vessel containing the formulated compound usually diluted with water to provide a suitable concentration of a present naphthalenamine.

The present naphthalenamine derivatives have also displayed systemic ectoparasiticidal activity. The compounds provided herein have the ability to permeate the tissues of a host animal to which one of the compounds has been administered. Insect parasites which then consume blood or other living tissues of the host animal are thereby killed. The compounds are administered by either oral or percutaneous routes and are preferably formulated prior to administration. Such formulations are well known to those skilled in the art, for example by dissolving the compound in one of several physiologically-acceptable carriers or diluents. Oral administration of a naphthalenamine may be performed by mixing the compound in the animals feed or drinking water, or by administering dosage forms such as tablets, capsules, boluses or implants. Percutaneous administration is conveniently accomplished by subcutaneous, intramuscular and the intravenous injection of an injectable formulation.

The term "ectoparasiticidally-effective amount," as defined herein, refers to an amount of a present naphthalenamine which kills or inactivates the insect. This amount will generally be from about 10,000 ppm to 1 ppm, more preferably from about 1000 ppm to 10 ppm, or 5 to 500 mg./kg.

The ectoparasiticidal activity of compounds employed in the present invention is illustrated by the following experiments.

EXPERIMENT 3

The test compounds were combined with bovine serum to provide a compound concentration of 20 ppm. Addition of further serum provided lower levels of active ingredient. Fifty first instar stage of black blowfly larvae were placed in a petri dish and subjected to the serum/compound solution. In a separate petri dish approximately 30 adult houseflies were combined with the medicated serum. Activity was determined by the number of dead organisms as compared to a control after 24 hours according to the following scale:

| Rating | Percent Dead |
|---|---|
| 0 | 0 |
| 1 | 1–49 |
| 2 | 50–74 |
| 3 | 75–89 |
| 4 | 90–99 |
| 5 | 100 |

The results of the blowfly larvae test appear in Table 3 while the results for the adult housefly appear below in Table 4.

TABLE 3

| | Blowfly Larvicide | |
|---|---|---|
| Example No. of Compound Tested | Concentration (ppm) | Rating |
| 1 | 10.0 | 0 |
| | 10.0 | 5 |

TABLE 3-continued

Blowfly Larvicide

| Example No. of Compound Tested | Concentration (ppm) | Rating |
|---|---|---|
| 2 | 10.0 | 5 |
| 3 | 10.0 | 5 |
|   | 10.0 | 2 |
| 4 | 10.0 | 5 |
|   | 10.0 | 0 |
| 5 | 20.0 | 0 |
|   | 10.0 | 0 |
|   | 10.0 | 0 |
| 6 | 10.0 | 5 |
|   | 10.0 | 3 |
|   | 10.0 | 0 |
| 7 | 10.0 | 5 |
|   | 10.0 | 5 |
|   | 10.0 | 5 |
|   | 10.0 | 0 |
| 8 | 10.0 | 5 |

TABLE 4

Housefly Adulticide

| Example No. of Compound Tested | Concentration (ppm) | Rating |
|---|---|---|
| 1 | 10.0 | 4 |
| 2 | 10.0 | 5 |
| 3 | 10.0 | 5 |
|   | 10.0 | 3 |
| 4 | 10.0 | 2 |
| 6 | 10.0 | 5 |
|   | 10.0 | 3 |
|   | 10.0 | 3 |
| 7 | 10.0 | 5 |
|   | 10.0 | 5 |
| 8 | 10.0 | 1 |

EXPERIMENT 4

A 0.5% solution of Example 1 of the present invention dissolved in 5 ml. of acetone was sprayed onto an area 6 inches in diameter on the side of a bovine (cow or steer). During the winter months the hair on the area is clipped to ¼ to ½ inch in length so that the flies can reach the skin to feed, but clipping is not necessary when the animals are in summer coat. During the test period the animals were confined in individual stanchions. Two sun lamps, one directed toward the treated spots on each side of a test animal, were turned on for a period of 4-hr. each day. Each lamp was about 2 meters from the floor and 1 meter from the animal and positioned so that all treated spots received about the same amount of radiation. Cages, made by soldering screen wire in a mason-jar ring, were used to confine adult stable flies, *Stomoxys calcitrans*, to the treated spots. Twenty-five 3- to 6-day-old female flies that had not fed for about 18 hr. were exposed in a cage to a spot for 20 minutes. The cage with the flies was then removed and placed in the laboratory at 27° C. and 60–70% relative humidity. The number of flies that had fed and the number that had been knocked down were recorded, a square of cotton soaked in blood diet was placed on each cage, and the flies were held for 24 hr. when mortality was recorded. Compounds were tested for both repellency and toxicity. Repellency was indicated when less than 20% of the flies have fed during the 20-minute exposure period. Toxicity was indicated when 90% or more of the flies are dead at 24 hr.

Example 1, as tested in the foregoing procedure, was ineffective at one day both as a toxicant and a repellent.

Typically, compounds that have exhibited systemic ectoparasiticidal activity, as has Example 1, have not exhibited activity in this screen. It is believed that this active agent was absorbed into the blood system of the animal therby significantly diluting its effect as a contact insecticide.

Systemic ectoparasitic activity of representative compounds employed in the present invention is illustrated by the following experiments.

EXPERIMENT 5

Certain compounds were tested in the following guinea pig systemic insecticide screen to evaluate their in vivo ectoparasiticidal efficacy.

The test compounds were first administered to guinea pigs by either oral or intraperitoneal routes. After 24 hours the animals were sacrificed and blood was taken from around the heart. The medicated blood serum was then added to individual petri dishes containing blowfly larvae and adult houseflies. After an additional 24 hours the number of dead insects were recorded according to the scale outlined in Experiment 3. These results appear below in Table 5.

TABLE 5

| Example No. of Compound Tested | Test Organism | Concentration mg./kg. | Route of Administration | Rating |
|---|---|---|---|---|
| 1 | Blowfly | 100 | oral | 0 |
|   | Larvae | 50 | IP | 0,0 |
|   | Adult | 100 | oral | 1,1,1 |
|   | Housefly | 50 | IP | 1,1,1,1 |
| 2 | Blowfly | 200 | oral | 0 |
|   | Larvae | 100 | IP | 0 |
|   | Adult | 200 | oral | 1 |
|   | Housefly | 100 | IP | 1 |

EXPERIMENT 6

The following method was used to determine the activity of certain naphthalenamines as animal systemic insecticides. White mice were artificially infested nasally, buccally, or ocularly with 5 newly-hatched larvae of Cuterebra sp. After 48 hours a plastic collar was placed around the neck of each male mouse, and the portion of the body behind the collar was dipped into 200 ml. of an emulsion of the test compound. A standard emulsifiable concentrate consists of 25 parts of the test compound, 10 parts Triton X-100, and 65 parts xylene. Four days after treatment, the skin of each mouse was examined carefully for encapsulated, live larvae. Effectiveness of the treatments was determined by comparing numbers of larvae encapsulated in treated mice with numbers in untreated mice. Usually 3 mice were treated at each concentration. Data is presented in Table 6 below as the percent of test compound in the formulation required to kill 50% of the larvae ($LC_{50}$) and 90% of the larvae ($LC_{90}$).

TABLE 6

| Example No. of Compound Tested | Percent of Test Compound in Formulation | |
|---|---|---|
|   | $LC_{50}$ | $LC_{90}$ |
| 1 | 0.069 | 0.23 |
| 6 | 0.059 | 2.08 |
| 7 | 0.040 | 0.17 |

What is claimed is:

1. A method for suppressing insects which comprises applying to a locus of the insects an insecticidally-effective amount of a compound of the formula

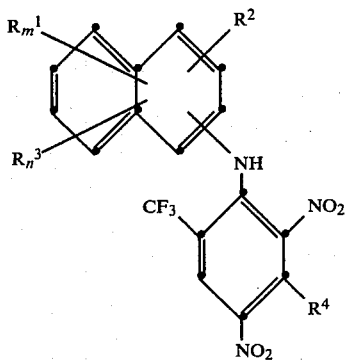

wherein:
$R^1$ is $C_1$–$C_4$ alkyl;
$R^2$ is halogen, phenyl, nitro, cyano, $C_1$–$C_4$ fluoroalkyl, $C_1$–$C_4$ fluoroalkoxy or $C_1$–$C_4$ fluoroalkylthio;
$R^3$ is halogen;
$R^4$ is hydrogen or halogen;
m is 0, 1 or 2; and
n is 0 or 1;
with the proviso that $R^2$ and the dinitroaniline moiety are on the same ring.

2. A method of claim 1 wherein m is 0.
3. A method of claim 2 wherein $R^4$ is hydrogen.
4. A method of claim 3 wherein n is 1.
5. A method of claim 4 wherein $R^2$ is halogen.
6. The method of claim 5 wherein the compound is 2,4-dibromo-N-[2,4-dinitro-6-(trifluoromethyl)phenyl]-1-naphthalenamine.
7. The method of claim 5 wherein the compound is 2-bromo-4-chloro-N-[2,4-dinitro-6-(trifluoromethyl)phenyl]-1-naphthalenamine.
8. A method of claim 3 wherein n is 0.
9. A method of claim 8 wherein $R^2$ is halogen.
10. The method of claim 9 wherein the compound is 4-chloro-N-[2,4-dinitro-6-(trifluoromethyl)phenyl]-1-naphthalenamine.
11. The method of claim 9 wherein the compound is 4-bromo-N-[2,4-dinitro-6-(trifluoromethyl)phenyl]-1-naphthalenamine.
12. A method of claim 8 wherein $R^2$ is nitro.
13. The method of claim 12 wherein the compound is 1-nitro-N-[2,4-dinitro-6-(trifluoromethyl)phenyl]-2-naphthalenamine.
14. The method of claim 12 wherein the compound is 4-nitro-N-[2,4-dinitro-6-(trifluoromethyl)phenyl]-1-naphthalenamine.
15. A method of claim 8 wherein $R^2$ is cyano.
16. The method of claim 15 wherein the compound is 4-cyano-N-[2,4-dinitro-6-(trifluoromethyl)phenyl]-1-naphthalenamine.
17. A method of claim 8 wherein $R^2$ is phenyl.
18. The method of claim 17 wherein the compound is 4-phenyl-N-[2,4-dinitro-6-(trifluoromethyl)phenyl]-1-naphthalenamine.
19. A method of killing insects which consume living tissues of a host animal which comprises orally or percutaneously administering to a host animal infested with such insects an ectoparasiticidally-effective amount of a compound of the formula

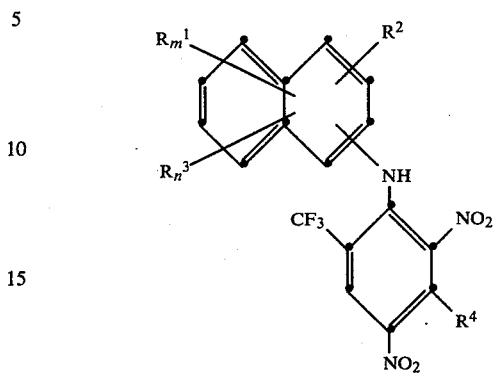

wherein:
$R^1$ is $C_1$–$C_4$ alkyl;
$R^2$ is halogen, phenyl, nitro, cyano, $C_1$–$C_4$ fluoroalkyl, $C_1$–$C_4$ fluoroalkoxy or $C_1$–$C_4$ fluoroalkylthio;
$R^3$ is halogen;
$R^4$ is hydrogen or halogen;
m is 0, 1 or 2; and
n is 0 or 1;
with the proviso that $R^2$ and the dinitroaniline moiety are on the same ring.

20. A method of claim 19 wherein m is 0.
21. A method of claim 20 wherein $R^4$ is hydrogen.
22. A method of claim 21 wherein n is 1.
23. A method of claim 22 wherein $R^2$ is halogen.
24. The method of claim 23 wherein the compound is 2,4-dibromo-N-[2,4-dinitro-6-(trifluoromethyl)phenyl]-1-naphthalenamine.
25. The method of claim 23 wherein the compound is 2-bromo-4-chloro-N-[2,4-dinitro-6-(trifluoromethyl)phenyl]-1-naphthalenamine.
26. A method of claim 21 wherein n is 0.
27. A method of claim 26 wherein $R^2$ is halogen.
28. The method of claim 27 wherein the compound is 4-chloro-N-[2,4-dinitro-6-(trifluoromethyl)phenyl]-1-naphthalenamine.
29. The method of claim 27 wherein the compound is 4-bromo-N-[2,4-dinitro-6-(trifluoromethyl)phenyl]-1-naphthalenamine.
30. A method of claim 26 wherein $R^2$ is nitro.
31. The method of claim 30 wherein the compound is 1-nitro-N-[2,4-dinitro-6-(trifluoromethyl)phenyl]-2-naphthalenamine.
32. The method of claim 30 wherein the compound is 4-nitro-N-[2,4-dinitro-6-(trifluoromethyl)phenyl]-1-naphthalenamine.
33. A method of claim 26 wherein $R^2$ is cyano.
34. The method of claim 33 wherein the compound is 4-cyano-N-[2,4-dinitro-6-(trifluoromethyl)phenyl]-1-naphthalenamine.
35. A method of claim 26 wherein $R^2$ is phenyl.
36. The method of claim 35 wherein the compound is 4-phenyl-N-[2,4-dinitro-6-(trifluoromethyl)phenyl]-1-naphthalenamine.

* * * * *